(12) United States Patent
Rabasco et al.

(10) Patent No.: US 7,619,017 B2
(45) Date of Patent: Nov. 17, 2009

(54) POLYMER EMULSIONS RESISTANT TO BIODETERIORATION

(75) Inventors: John Joseph Rabasco, Allentown, PA (US); Dennis Sagl, Fogelsville, PA (US)

(73) Assignee: Wacker Chemical Corporation, Adrian, MI (US)

( * ) Notice: Subject to any disclaimer, the term of this patent is extended or adjusted under 35 U.S.C. 154(b) by 776 days.

(21) Appl. No.: 10/441,806

(22) Filed: May 19, 2003

(65) Prior Publication Data

US 2004/0235982 A1    Nov. 25, 2004

(51) Int. Cl.
  C08K 5/34    (2006.01)
  C08K 5/17    (2006.01)
  C09D 5/16    (2006.01)
(52) U.S. Cl. ............... 523/122; 524/238; 524/239; 524/240; 524/99
(58) Field of Classification Search ............ 523/122; 524/238, 239, 240
  See application file for complete search history.

(56) References Cited

U.S. PATENT DOCUMENTS

| 4,158,053 | A | | 6/1979 | Greene et al. | |
|---|---|---|---|---|---|
| 5,859,112 | A | * | 1/1999 | Overbeek et al. | 524/460 |
| 6,066,674 | A | | 5/2000 | Hioki et al. | 514/643 |
| 6,303,557 | B1 | | 10/2001 | Colclough | |
| 6,383,505 | B1 | | 5/2002 | Kaiser et al. | 424/407 |
| 6,583,181 | B1 | | 6/2003 | Chiang et al. | |
| 2002/0099113 | A1 | | 7/2002 | Rabasco et al. | 523/122 |
| 2002/0183233 | A1 | | 12/2002 | Mitra et al. | 510/438 |
| 2005/0192199 | A1 | * | 9/2005 | Cartwright et al. | 510/420 |

FOREIGN PATENT DOCUMENTS

| EP | 1153544 | | 11/2001 |
|---|---|---|---|
| EP | 1 188 377 | A1 | 3/2002 |
| JP | 2001-302415 | A | 10/2001 |

\* cited by examiner

Primary Examiner—Kriellion A Sanders
(74) Attorney, Agent, or Firm—RatnerPrestia

(57) ABSTRACT

This invention is directed to a method of preserving polymer emulsions against biodeteriogenic microbe attack and spoilage by combining with the polymer emulsions selected cationic compounds and an ethylenediamine acid compound. The polymer emulsions contain surfactants and/or anionic constituents. It is also directed to polymer emulsion compositions, that are resistant to spoilage by biodeteriogenic microbes, containing surfactants and/or anionic constituents, an ethylenediamine acid compound, and cationic compounds.

23 Claims, No Drawings

POLYMER EMULSIONS RESISTANT TO BIODETERIORATION

BACKGROUND OF THE INVENTION

Water based polymer emulsions (latex emulsions) are susceptible to microbial contamination resulting in product spoilage. Polymer emulsions are dispersions of fine organic polymer particles in water. These polymer particles are suspended and stabilized in an aqueous environment with additional organic substrates, such as surfactants and protective colloids. Surfactants, protective colloids, such as poly(vinyl alcohol) and hydroxyethyl cellulose, thickeners and other additives, and the polymer itself all provide a supply of carbon nutrition for microorganisms to metabolize. Polymer emulsions are therefore susceptible to spoilage due to microbial attack and propagation. Standard industrial practices combat such product biodeterioration by the addition of various industrial biocides (antimicrobial agents) directly after the manufacturing process. Examples of commonly used industrial biocides are: 1,2-benzisothiazolin-3-one (BIT), and a blend of 5-chloro-2-methyl-4-isothiazolin-3-one (CIT) and 2-methyl-4-isothiazolin-3-one (MIT). Examples of other biocides commonly used for polymer emulsion preservation include 1,2-dibromo-2,4-dicyanobutane (DBDCB), 2,2-dibromo-3-nitrilo-propionamide (DBNPA), 2-bromo-2-nitro-1,3-propanediol (BNPD), aldehyde derivatives, formaldehyde releasing agents, hydantoins, and chlorinated aromatics.

These commonly used biocides are usually adequate to preserve various types of polymer emulsions against most industrial spoilage from bacteria and fungi. However, polymer emulsions are more susceptible to spoilage by certain types of microbes. For example, biodeteriogenic microbes that can survive in acidic environments and/or that metabolize alcohols, such as *Gluconoacetobacter liquefaciens* (GABL), have begun to emerge and thrive in polymer emulsions, even in the presence of commonly used industrial biocides. Biodeteriogenic microbes include bacteria and fungi that can adversely affect the commercial value of products and materials. Some biodeteriogenic microbes have become so well adapted to the environment present in these emulsions that the standard industrial biocides are inadequate to prevent product spoilage over the entire product shelf life; e.g., 6 to 12 months. A significant rise in polymer emulsion biodeterioration problems has resulted in a need to identify more effective preservative systems.

It is known that VOC's (volatile organic compounds) in polymer emulsions exert some level of a bacteriostatic, it not bacteriocidal, effect, which can inhibit the growth of biodeteriogenic microbes. Examples of VOC's present in polymer emulsions are unreacted monomers, such as vinyl acetate, acetic acid, methanol, acetaldehyde, and formaldehyde. Recent developments in polymer emulsion technology, in response to regulatory issues and environmental concerns, have lead to reductions in residual VOC. Such VOC reductions impact polymer emulsions in many ways from a microbiological perspective. For example: 1) it creates an emulsion environment more conducive to microbial growth, 2) it may permit the emergence of new microorganisms that find the new emulsion environment more hospitable, 3) it poses additional challenges to current preservative technologies, and 4) it creates the need for new preservation methods to prevent biodeterioration over the product's shelf life.

Although there are a significant number of biocides that can kill microorganisms effectively and can provide very good preservation for polymer emulsions and other industrial products, only a limited number of these exhibit acceptably low toxicity to higher organisms, e.g., humans. The choice of effective biocides that can be added to polymer emulsions becomes even more limited when United States Food and Drug Administration (FDA) clearances are required for the polymer emulsion end use. Many polymer emulsions are used to manufacture consumer goods, such as adhesives and papers for food packaging, diapers, paper towels, baby wipes, and feminine hygiene products. As a result of such contact with skin and indirect contact with foods, the polymer emulsions used in these applications must have the appropriate FDA clearances. These FDA clearances are based on favorable toxicological profiles, including no skin sensitization. In order for a polymer emulsion to receive the necessary FDA clearances, all of its constituents, including the preservative technology, must meet FDA's rigorous toxicological criteria when used at concentrations required for satisfactory performance in the polymer emulsion. FDA-approved biocides have use level restrictions. In some cases, the minimum biologically effective concentration is greater than the maximum allowable use level. Typically, this results in premature product biocontamination and biodeterioration. Additionally, microorganisms continue to evolve and new microorganisms are beginning to appear that exhibit resistance to some of the more common industrial biocidal agents, particularly at the allowable use level. A tightening regulatory environment, specific consumer good manufacturing specifications, public concern, and product liability further complicates biocide selection and use. For example, isothiazolinones are widely used antimicrobial agents for many consumer products, but their known skin sensitization property causes concern among many consumer goods manufacturers. Such health concerns and microbial resistance are leading to a search for preservation alternatives and new preservation approaches. Cationic compounds, such as quaternary ammonium compounds, are well known in the antimicrobial art and are widely used as disinfectants for surfaces. For example, they are used to disinfect floors, walls, countertops, equipment surfaces, food contact surfaces, and the like in hospitals, schools, nursing homes, restaurants, and residential homes. Furthermore, combinations of detergents with cationic compounds are widely used formulations for cleaning and disinfecting or sanitizing such surfaces with a single product. Cationic compounds are also used to inhibit the growth of algae and microorganisms in water, such as in swimming pools. Cationic compounds have been utilized on a limited basis for the preservation of industrial products and to prevent microbial growth in aqueous systems.

Examples of uses of cationic compounds in disinfectant compositions and in preservatives for polymer emulsions are discussed below:

U.S. Pat. No. 6,066,674 (Hioki et al., 2000) teaches a germicidal-disinfectant detergent composition composed of a cationic germicide, a metal chelating agent, and at least one surfactant selected from anionic, nonionic, and amphoteric surfactants. Metal chelating agents, such as sodium EDTA, sodium citrate, and sodium tripolyphosphate, are reported to be necessary to maintain germicidal activity of the cationic species in the presence of anionic surfactants.

US 2002/0099113 A1 (Rabasco et al., 2002) teaches a method of preserving colloid-stabilized polymer emulsions against microbial attack and spoilage using selected cationic compounds. It is also directed to compositions containing colloid-stabilized polymer emulsions and cationic compounds that are resistant to contamination with biodeteriogenic microbes. The polymer emulsions contain little or no nonionic or anionic surfactants and little or no anionic constituents.

U.S. Pat. No. 6,383,505 B1 (Kaiser et al., 2002) discloses an antimicrobial lotion for topical use which comprises an oil-in-water emulsion with a dispersant of emollient droplets in an oil phase and an antimicrobial agent in a water phase. It is reported that a combination of anionic and nonanionic surfactants stabilize the emulsion and maintain a cationic antimicrobial agent primarily in the water phase.

A need remains for a method of protecting polymer emulsions against product biodeterioration by microbes, especially polymer emulsions stabilized with surfactants and/or containing anionic constituents, and those with low VOC's.

BRIEF SUMMARY OF THE INVENTION

This invention is directed to a method of protecting polymer emulsions against biodeteriogenic microbe attack and spoilage by combining the polymer emulsions with selected cationic compounds and an ethylenediamine acid compound (referred to as EDA compound) having the structure:

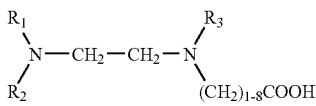

wherein $R_1$, $R_2$, and $R_3$ are, independently, H, a $C_1$-$C_{12}$ alkyl, or —$(CH_2)_{1-8}COOH$. The EDA compound can also be a mono-, di-, tri- or tetra-salt of the compounds of the above structure. Examples of salts are: alkali metal salts, alkaline earth metal salts, ammonium or ammonium derived salts having the structure:

wherein $R_4$, $R_5$, $R_6$, and $R_7$ are independently, H or $C_{1-12}$ alkyl; provided the salt is soluble in water. Preferred compounds are ethylenediamine tetraacetic acid and its mono-, di-, tri- and tetra-salts; especially the tetrasodium salt of ethylenediamine tetraacetic acid. More specifically, this invention is directed to a method for preserving polymer emulsions against biodeteriogenic microbe attack and spoilage using the selected cationic compounds in combination with the above EDA compounds and their salts. The polymer emulsions contain surfactants and/or anionic constituents.

The invention is also directed to polymer emulsion compositions that are resistant to biodeteriogenic microbe attack and spoilage. The polymer emulsion compositions contain surfactants and/or anionic constituents, EDA compounds, and cationic compounds.

Examples of cationic compounds that are effective in preserving the polymer emulsions against biodeteriogenic microbes when used in combination with EDA compounds are: substituted pyridinium salts such as cetylpyridinium chloride, tetraalkylsubstituted ammonium salts such as didecyldimethylammonium chloride, and benzalkonium derivatives such as $C_{12}$-$C_{18}$ alkyldimethyl benzalkonium chlorides, benzethonium chloride, chlorhexidine, polymeric guanides and biguanides, such as poly(hexamethylenebiguanide) hydrochloride, and other polymeric cationic compounds such as polyvinyl pyridine and polyethyleneimine. The cationic compounds when used in combination with EDA compounds are also particularly effective in preserving polymer emulsions with low levels of VOC (i.e., less than 100 ppm VOC).

The combination of EDA compounds with cationic compounds are effective as stand-alone preservatives, exhibiting a broad spectrum of microbicidal activity against bacteria and fungi for an extended period of time, or can also be used in combination with other biocides, such as isothiazolinone derivatives.

The polymer emulsion compositions of this invention can be blended and formulated with other raw materials for use in preparation of adhesives, architectural coatings, paper coatings, nonwoven binders, etc. For example, although the polymer emulsion compositions of this invention may be used neat for adhesive applications, such polymer emulsion compositions are often formulated depending upon the specific end use.

It may be required to add additional amounts of the cationic biocide and EDA compounds to compensate for the dilution by formulation additives in order to produce a water-based adhesive or coating composition that is resistant to biodeteriogenic microbe contamination.

DETAILED DESCRIPTION OF THE INVENTION

Polymer emulsions of this invention are dispersions of synthetic polymers and copolymers in aqueous media. The basic raw materials used to manufacture the polymer emulsions are monomers, initiators, and stabilizers. Examples of monomers include vinyl acetate, ethylene and other olefins, diolefins such as butadiene, various alkyl acrylates, various alkyl methacrylates, styrene, vinyl chloride, vinyl esters, acrylamides, methacrylamides, N-methylolacrylamides, maleates, and others known in the art. Examples of polymer emulsions for purposes of this invention include emulsions of poly(vinyl acetate), poly(vinyl acetate) copolymers such as poly(vinyl acetate-co-ethylene) (VAE), poly(vinyl acetate-acrylics) such as poly(vinyl acetate-butyl acrylate) and poly (vinyl acetate-(2-ethyl)hexyl acrylate), polyacrylics, polymethacrylics, poly(styrene-acrylics), wherein acrylics can include $C_3$-$C_{10}$ alkenoic acids, such as acrylic acid, methacrylic acid, crotonic acid and isocrotonic acid and their esters, other polystyrene copolymers, poly(vinyl chloride-co-ethylene) copolymers, and the like. These polymer emulsions can be stabilized with various surfactants known in the art or with protective colloids, such as hydroxyethyl cellulose or poly(vinyl alcohol), and others known in the art. Polymer emulsions particularly suitable for this invention contain nonionic and/or anionic surfactants, and/or contain anionic constituents.

Examples of nonionic surfactants are the Igepal surfactants supplied by Rhone-Poulenc. The Igepal surfactants are members of a series of alkylphenoxy-poly(ethyleneoxy)ethanols having alkyl groups containing from about 7-18 carbon atoms, and having from about 4 to 100 ethyleneoxy units, such as the octylphenoxy poly(ethyleneoxy)ethanols, nonylphenoxy poly(ethyleneoxy)ethanols, and dodecylphenoxy poly(ethyleneoxy)ethanols. Other examples of nonionic surfactants include ethoxylated aliphatic alcohols, polyoxyalkylene derivatives of hexitol (including sorbitans, sorbides, manitans, and mannides) anhydride, partial long-chain fatty acid esters, such as polyoxyalkylene derivatives of sorbitan monolaurate, sorbitan monopalmitate, sorbitan monostearate, sorbitan tristearate, sorbitan monooleate and sorbitan trioleate.

Common examples of anionic surfactants include sulfosuccinates, alkyl or alkylated aromatic sulfates and phosphonate or sulfate esters of ethoxylated alkyl alcohols or alkylated aromatic phenols.

Examples of anionic constituents include acrylic acid, sodium vinyl sulfonate, maleates, methacrylic acid, crotonic acid, 2-acrylamido-2-methylpropanesulfonic acid, and other monomers known in the art, as well as anionic polymer chain ends introduced by the use of initiators such as persulfate salts. Polymer emulsions with less than 1000 ppm VOC's are also particularly suitable for this invention. Among the VOC's present in polymer emulsions are unreacted monomers, acetic acid, methanol, acetaldehyde, and formaldehyde.

The polymer emulsions can be formulated for other end uses such as adhesives, architectural coatings, paper coatings, and binders, such as nonwoven binders. When formulated for adhesive compositions, the polymer emulsions can be present at levels ranging from 60 to 90 parts by weight of the total formulation. Common additives used in the formulation of adhesive compositions include, plasticizers, defoamers, thickeners, dispersants, crosslinkers, humectants, tackifiers, polyvinyl alcohol, and fillers.

Representative plasticizers include glycols, such as dipropylene glycol, dibenzoate types, such as dipropylene glycol dibenzoate and diethylene glycol dibenzoate, phthalates, such as dibutyl phthalate, and liquid polyesters, such as triethylene glycol polyester of benzoic acid and phthalic acid, and others known in the water-based adhesion art. The plasticizer is typically used at levels ranging from 2 to 30 parts by weight of the total formulation.

Representative defoamers include silicon or hydrocarbon based materials. The defoamer is typically used at levels up to 1 part by weight of the total formulation.

Representative thickeners include, casein, fumed silica, guar gum, bentonite, oliginates, starches, hydroxyethyl cellulose, other cellulosics, polyether polyols, and other thickeners known in the water-based adhesion art. Thickeners are typically used at levels up to 5 parts by weight of the total formulation.

Representative crosslinkers include dialdehydes, such as glutaraldehyde, metals, such as zinc and zirconium, melamine formaldehyde resins, diepoxide and epoxy resins. Crosslinkers are typically used at levels up to 10 parts by weight of the total formulation.

Representative humectants include, calcium chloride, glycols, glycerine, ureas, sorbitol, and others known in the water-based adhesion art. Humectants are typically incorporated at levels up to 20 parts by weight of the total formulation.

Representative tackifiers include, gum rosin, ester gum, hydrocarbon resins, hydrogenated rosin, tall oil rosins, terpene resins, and others known in the water-based adhesion art. Tackifiers are typically used in their dispersion form and are used at levels up to 35 parts by weight of the total formulation in adhesive compositions.

Representative fillers include, calcium carbonate, clay, mica, silica, talc, and others known in the water-based adhesion art. Fillers are typically used at levels up to 40 parts by weight of the total formulation.

When formulated for architectural coating compositions, the polymer emulsions can be present at levels ranging from 25 to 75 parts by weight. Common additives used in the formulation of architectural coating compositions include plasticizers, defoamers, thickeners, pH control agents, coalescing solvents, freeze-thaw additives, in can and dry film preservatives, pigments and fillers and anionic and nonionic surfactants Representative plasticizers in architectural coating compositions include benzoate esters. Plasticizers are typically used at levels ranging from 1 to 2 parts by weight of the total formulation.

Representative defoamers in architectural coating compositions include mineral oil based defoamers and hydrophobic silica. Defoamers are typically used at levels ranging from 0.3 to 0.6 parts by weight of the total formulation.

Representative thickeners in architectural coating compositions include hydroxyethylcellulose and hydrophobically modified hydroxyethylcellulose, which have typical use levels of 0.5 to 1.0 parts by weight of the total formulation. In addition, copolymers of ethyl acrylate/acrylic acid and also hydrophobically modified urethane ethoxylates are used as thickeners. These thickeners are typically used at levels ranging from 1.5 to 3.0 parts by weight of the total formulation.

Representative dispersants in architectural coating compositions include poly(acrylic acid), poly(methacrylic acid), and copolymers of diisobutylene/maleic anhydride. Dispersants are typically used at levels ranging from 0.8 to 1.0 parts by weight of the total formulation.

Representative pH control agents in architectural coating compositions include amino methyl propanol and ammonium hydroxide. The pH control agents are typically used at levels ranging from 0.2 to 0.3 parts by weight of the total formulation.

Representative coalescing solvents in architectural coating compositions include 2,2,4-trimethyl isobutyrate and ethylene glycol dibutyl ether. Coalescing solvents are typically used at levels ranging from 1 to 2 parts by weight of the total formulation.

Representative freeze-thaw additives in architectural coating compositions include ethylene glycol and propylene glycol. Freeze-thaw additives are typically used at levels ranging from 1 to 4 parts by weight of the total formulation.

Representative preservatives in architectural coating compositions include 1,2-benzisothiazolin-3-one, blends of 2-chloro-2-methyl-4-isothiazolin-3-one and 2-methyl-4-isothiazolin-3-one, formaldehyde releasing agents, 2-octyl-4-isothiazolin-3-one and zinc pyrithione. Preservatives are typically used at levels up to 0.2 parts by weight of the total formulation.

Representative pigments and fillers in architectural coating compositions include titanium dioxide, calcium carbonate, clay, mica, silica, talc, and others known in the water-based architectural coating art. Titanium dioxide is the most common pigment used in architectural coatings, and it is typically used at levels ranging from 8 to 25 parts by weight of the total formulation.

Representative nonionic surfactants in architectural coating compositions include alkyl phenol ethoxylates. Nonionic surfactants are typically used at levels ranging from 0.3 to 0.6 parts by weight of the total formulation.

Representative anionic surfactants used in architectural coating compositions include dioctyl sulfosuccinate, dodecylbenzenesulfonate and phosphate esters and sulfate esters of alkyl phenols. Anionic surfactants are typically used at levels up to 0.2 parts by weight of the total formulation.

Microbial contamination of polymer emulsions can lead to a range of effects, including color changes, odors, viscosity changes, pH changes, and visible surface growth. It is known in the art that polymer emulsions are susceptible to contamination by a broad range of biodeteriogenic microbes. Examples of microorganisms found to contaminate polymer emulsions include, *Aeromonas hydrophilia, Alcaligenes faecalis, Corynebacterium ammoniagenes, Enterobacter aerogenes, Escherichia coli, Klebsiella pneumoniae,*

*Pseudomonas aeruginosa, Proteus vulgaris, Providencia rettgeri, Pseudomonas stutzeri, Shewanella putrefaciens, Serratia liquefaciens, Acinetobacter baumannii, Burkholderia cepacia, Chryseobacterium meningosepticum, Sphingobacterium spiritivorum, Ralstonia pickettii, Gluconoacetobacter liquefaciens, Geotrichum candidum, Aspergillus* species, *Sporothrix* species, *Trichoderma viride, Cladosporium* species, *Rhodoturula glutinis, Candida guillermondi, Penicillium* species, and *Candida tropicalis*.

It has been found in this invention that cationic biocides in combination with EDA compounds are effective in preserving polymer emulsions, that contain anionic constituents and/or have been emulsified with anionic and/or nonionic surfactants, against microbial spoilage due to various bacterial species.

Acceptable cationic compounds for the preservation of the polymer emulsions of this invention include substituted pyridinium salts such as cetylpyridinium chloride (CPC) in which the substitution is an alkyl, a cycloalkyl, or an aryl group of 2 to 18 carbons, tetraalkylsubstituted ammonium salts such as didecyldimethylammonium chloride in which the alkyl groups are independently 1 to 18 carbons, and alkyldimethyl benzalkonium chloride in which the alkyl is 1 to 18 carbons, benzethonium chloride, poly(hexamethylenebiguanide) hydrochloride and other biguanides, chlorhexidine, polymeric cationic compounds such as poly(hexamethylenebiguanide) hydrochloride, and the like. Preferred cationic derivatives include tetrasubstituted quaternary ammonium derivatives, biguanides, polymeric biguanides, and alkylpyridinium salts in which the alkyl group contains 2 to 18 carbons. These cationic biocides are ineffective preservatives when used without EDA compounds in these polymer emulsion systems.

The EDA compounds of this invention can be made by methods well known in the art. Examples are: the reaction of ethylenediamine, formaldehyde and sodium cyanide and the reaction of ethylenediamine with chloroacetic acid. Salts of EDA compounds are generated by reaction of compounds prepared in this manner with the appropriate bases. Examples of commercially available EDTA are Versene® EDTA from Dow Chemical and Trilon® and Sequestrene® EDTA from BASF Corp.

EDA and the cationic compounds can be mixed with the polymer emulsion at any point during the polymer emulsion manufacturing process; preferably, the cationic compound is added to the polymer emulsion as the last additive in the post-manufacturing process. The order of addition of EDA compound and the cationic compound to the polymer emulsion is not critical, preferably EDA compound is added to the polymer emulsions first, followed by the cationic compound. The total amount or dosage of the cationic compound that is added to a polymer emulsion for preservation against microbial contamination can range from 10 ppm to 1 wt %, preferably 50 ppm to 500 ppm, based on the wet weight of the polymer emulsion. The total amount or dosage of EDA compound that is added to a polymer emulsion for preservation against microbial contamination can range from 10 ppm to 1 wt %, preferably 50 ppm to 5000 ppm, and most preferably 50 ppm to 500 ppm, based on the wet weight of the polymer emulsion.

The EDA compound/cationic compound combinations of this invention can be used alone or together with other known industrial biocides; for example, BIT, CIT, MIT, DBDCB, DBNPA, DNPD, aldehyde derivatives, such as glutaraldehyde and formaldehyde, formaldehyde releasing agents, such as dimethyloldimethyl hydantoin, imidazolidinyl urea derivatives, polymethoxy bicyclic oxazolidine, and 1-(3-chloroallyl)-3,5,7-triaza-1-azoniaadamantane hydrochloride, hydantoins, phenols, such as sodium o-phenyl phenylate, and chlorinated aromatics, such as p-chloro-m-cresol, and chloroxylenol.

The invention will be further clarified by a consideration of the following examples, which are intended to be purely exemplary of the invention.

The preservative efficacy of several cationic compounds, with and without an ethylenediamine tetraacetic acid (EDTA) adjuvant, was examined by adding various dosage levels of the compounds to VAE polymer emulsions, some of which contain less than 1000 ppm vinyl acetate monomer. The resulting polymer emulsions were then subjected to stringent biochallenge testing, the details of which are described below.

EXAMPLE 1

The following procedure was used to assess the preservative efficacy of several cationic compounds in an anionic surfactant stabilized VAE copolymer emulsion containing less than 1000 ppm vinyl acetate monomer:

Test Microorganisms

*Aeromonas hydrophilia, Alcaligenes faecalis, Corynebacterium ammoniagenes, Enterobacter aerogenes, Escherichia coli, Klebsiella pneumoniae, Pseudomonas aeruginosa, Proteus vulgaris, Providencia rettgeri, Pseudomonas stutzeri, Shewanella putrefaciens, Serratia liquefaciens, Acinetobacter baumannii, Burkholderia cepacia, Chryseobacterium meningosepticum, Sphingobacterium spiritivorum, Ralstonia pickettii*, and *Gluconoacetobacter liquefaciens*.

Mixed Bacterial Pool Inoculum Preparation

Each bacterial culture was individually grown on nutrient agar slants, except GABL was grown on potato dextrose agar slants, by inoculating the agar surfaces. The nutrient agar slants were incubated for 24-48 hours at 30° C. and the potato dextrose agar slants were incubated for 48-72 hours at 25° C. After this incubation period, the cells were harvested using quarter strength Ringers solution to wash the bacterial colonies off the agar surface. The washings from all of the slants were combined into one sterile, Erlenmeyer flask. The number of slants and the amount of Ringers solution used to wash off the bacterial colonies is adjusted during the procedure to obtain a final mixed microbial viable count in the range of $10^8$-$10^{10}$ CFU/mL.

Rapid Automated Bacterial Impedance Technique (RABIT), supplied by Microbiology International, and manufactured by Don Whitley Scientific, Ltd. utilizes the principal of impedance microbiology to detect and assess microbial activity in a given sample. Using the RABIT, microbial metabolism is monitored by measuring the amount of carbon dioxide produced by actively respiring microorganisms. The electrodes in the RABIT test cells are partially covered with alkaline agar containing potassium hydroxide. As inoculated test samples are monitored on the RABIT, carbon dioxide produced from microbial metabolism is absorbed by the alkaline agar resulting in a change in conductivity. Conductivity is monitored with time and the time to reach a pre-specified rate of reduction in conductivity is termed the time to detection (TTD). Therefore, the shorter the TTD, the higher the number of microorganisms present. Failure can be defined as three successive decreases in conductivity equal to or greater than a pre-specified value (−10 microSiemens is recommended by the manufacturer) at any time during the 72 hour RABIT monitoring period. Alternatively, failure can be defined as a pre-specified total change in conductivity.

Biochallenge Test Procedure

Samples (50 g each) of each test emulsion containing a test antimicrobial agent were inoculated with 1.0 mL of the mixed bacterial inoculum. After mixing well, the samples were then placed in a 30° C. incubator. After 1, 2, and 6 days of incubation, each sample was streak plated onto nutrient agar and potato dextrose agar to assess the level of surviving microorganisms. The nutrient agar plates were incubated at 30° C. for 48 hours before assessing the growth. The potato dextrose agar plates were incubated at 25° C. for 48-72 hours before assessing the growth. On the seventh day of incubation, each test emulsion sample was inoculated again with a freshly prepared mixed bacterial inoculum, mixed well, then placed back into the incubator. The samples were again streak plated onto nutrient agar and potato dextrose agar after incubating for 1, 2, and 6 days since the second inoculation. On the fourteenth day after the test was initiated, the test emulsions were inoculated a third time with another freshly prepared mixed bacterial inoculum and then placed back into the incubator. The samples were again streak plated onto nutrient agar and potato dextrose agar after 1, 2, 6, and 13 days of incubation since the third inoculation to assess surviving microorganisms. Test failure is defined as a microbial viable count >300 CFU/10 μL observed from the nutrient agar or potato dextrose agar streak plate assessments.

Biochallenge Test Procedure Via the Rabit

A small amount of a microbial nutrient (typically yeast extract) was added to each emulsion test sample (50 g) containing a test antimicrobial agent. The resulting samples were then inoculated with 1.0 mL of the mixed bacterial inoculum. After mixing well, an aliquot (5 g) of each test sample was placed into separate RABIT indirect conductivity tubes. The indirect conductivity tubes were then placed into the RABIT incubator modules set at 30° C. and the conductivity changes monitored for up to 72 hours. The remainder of each test sample was stored in a 30° C. incubator during the RABIT monitoring period. At the completion of the RABIT monitoring period, the aliquot samples were placed back into their respective sample containers. Each test sample was then re-inoculated with a freshly prepared mixed bacterial inoculum. After mixing well, an aliquot (5 g) of each test sample was again placed into fresh RABIT indirect conductivity tubes and monitored on the RABIT as before. This inoculation and RABIT conductivity monitoring procedure was repeated every three to four days until sample failure or until several inoculations were passed without failure.

Table 1 shows the preservative efficacy of various types of cationic compounds, with and without the addition of EDTA salt (tetrasodium salt of ethylenediamine tetraacetic acid) or other metal chelating agents, to control and inhibit the growth of bacteria in AIRFLEX® 192 VAE copolymer emulsion having a $T_g$ of ~10° C. and stabilized with anionic surfactants and containing less than 1000 ppm vinyl acetate monomer. It is clear from the data that there are dramatic differences in preservative efficacy in this polymer emulsion environment depending upon the presence of EDTA. For example, a dosage of 300 ppm didecyldimethylammonium chloride exhibits no preservative efficacy by failing the biochallenge test immediately after the first inoculation with the mixed bacterial inoculum. Similar dosages of poly(hexamethylenebiguanide) hydrochloride, CPC (an active antimicrobial agent found in over the counter mouthwashes), and benzalkonium derivatives were just as ineffective. EDTA and other metal chelating agents by themselves are also inadequate. However, when these same cationic compounds are used in conjunction with EDTA, unexpectedly, preservative efficacy is achieved and these biocidal combinations provide excellent protection to the polymer emulsion against spoilage due to bacterial contaminants. These results were unexpected based on the prior art which teaches that other metal chelating agents, such as citric acid and maleic acid, are as effective as EDTA; however, they do not exhibit potentiation of the cationic compounds of this invention.

TABLE 1

Mixed Bacterial Biochallenge Test Results in AIRFLEX 192 VAE Polymer

| Biocide | Biocide Dosage* | Inoculations Passed |
|---|---|---|
| Blank (no biocide) | 0 | 0 |
| EDTA salt | 1000 ppm | 0 |
| Citric acid, sodium salt | 300 ppm | 0 |
| Trisodium phosphate | 300 ppm | 0 |
| Maleic acid, sodium salt | 300 ppm | 0 |
| Salicylic acid, sodium salt | 300 ppm | 0 |
| DGH | 400 ppm | 0 |
| DGH/EDTA salt | 300/300 ppm | 0 |
| CPC | 300 ppm | 0 |
| CPC/EDTA salt | 300/300 ppm | 1 |
| Vantocil ® IB Poly(hexamethylenebiguanide) hydrochloride | 500 ppm | 0 |
| Vantocil IB/EDTA salt | 300/250 ppm | ≧3 |
| Vantocil IB/Maleic acid, sodium salt | 300/300 ppm | 0 |
| Vantocil IB/Citric acid, sodium salt | 300/300 ppm | 0 |
| Vantocil IB/Ethylenediamine diacetic acid, disodium salt | 300/300 ppm | 1 |
| Vantocil IB/Nitrilotriacetic acid, trisodium salt | 300/300 ppm | 0 |
| Vantocil IB/Nitrilotriphosphonic acid, trisodium salt | 300/300 ppm | 0 |
| BTC ® 824 $C_{12}$-$C_{18}$ -Alkyldimethyl benzalkonium chlorides | 300 ppm | 0 |
| BTC 824/EDTA salt | 300/300 ppm | ≧3 |
| BTC 1010 Didecyldimethylammonium chloride | 300 ppm | 0 |
| BTC 1010/EDTA salt | 300/250 ppm | ≧3 |
| BTC 1010/Ethylenediamine diacetic acid, disodium salt | 300/300 ppm | 1 |
| BTC 1010/Maleic acid, sodium salt | 300/300 ppm | 0 |
| BTC 1010/Citric acid, sodium salt | 300/300 ppm | 0 |
| BTC 1010/Nitrilotriacetic acid, trisodium salt | 300/300 ppm | 0 |
| BTC 1010/Nitrilotriphosphonic acid, trisodium salt | 300/300 ppm | 0 |

*Active ingredient
BTC 1010 and 824 supplied by Stepan Co.;
Vantocil IB supplied by Avecia Biocides;
EDTA salt = tetrasodium salt of EDTA;
DGH = n-dodecylguanidine hydrochloride

EXAMPLE 2

The biochallenge test procedures were followed as described in Example 1. Table 2 shows the preservative efficacy of various types of cationic compounds, with and without the addition of EDTA salt (ethylenediamine tetraacetic acid, tetrasodium salt) or other metal chelating agents, to control and inhibit the growth of bacteria in AIRFLEX 410 VAE copolymer emulsion having a $T_g$ of ~4° C., stabilized with nonionic surfactants and containing less than 1000 ppm vinyl acetate monomer. It is clear from the data that there are dramatic differences in preservative efficacy in this polymer emulsion environment depending upon the presence or absence of EDTA salt. For example, a dosage of 300 ppm didecyldimethylammonium chloride exhibits no preservative efficacy by failing the biochallenge test immediately after the first inoculation with the mixed bacterial inoculum. Similar dosages of poly(hexamethylenebiguanide) hydrochloride, CPC (an active antimicrobial agent found in over the counter mouthwashes), and benzalkonium derivatives were just as ineffective. EDTA salt and other metal chelating agents by themselves are also inadequate. However, when these same cationic compounds are used in conjunction with EDTA salt, unexpectedly, preservative efficacy is achieved and these biocidal combinations provide excellent protection to the polymer emulsion against spoilage due to bacterial contaminants. These results are unexpected since, contrary to teachings in the prior art, other metal chelating agents, such as citric acid and maleic acid, do not exhibit potentiation of the cationic compounds in this polymer emulsion.

TABLE 2

Mixed Bacterial Biochallenge Test Results in AIRFLEX 410 VAE polymer

| Biocide | Biocide Dosage* | Inoculations Passed |
|---|---|---|
| Blank (no biocide) | 0 | 0 |
| EDTA salt | 1000 ppm | 0 |
| DGH | 300 ppm | 0 |
| DGH/EDTA salt | 150/500 ppm | 0 |
| CPC | 300 ppm | 0 |
| CPC/EDTA salt | 200/200 ppm | ≧3 |
| Vantocil ® IB Poly(hexamethylenebiguanide) hydrochloride | 500 ppm | 0 |
| Vantocil IB/EDTA salt | 100/100 ppm | ≧3 |
| Vantocil IB/Maleic acid, sodium salt | 200/200 ppm | 0 |
| Vantocil IB/Citric acid, sodium salt | 200/200 ppm | 0 |
| Vantocil IB/Ethylenediamine diacetic acid, disodium salt | 200/200 ppm | 1 |
| Vantocil IB/Nitrilotriacetic acid, trisodium salt | 200/200 ppm | 0 |
| Vantocil IB/Nitrilotriphosphonic acid, trisodium salt | 200/200 ppm | 0 |
| BTC 1010 Didecyldimethylammonium chloride | 300 ppm | 0 |
| BTC 1010/EDTA salt | 200/200 ppm | ≧3 |
| BTC 1010/Ethylenediamine diacetic acid, disodium salt | 200/200 ppm | 0 |
| BTC 1010/Maleic acid, sodium salt | 200/200 ppm | 0 |
| BTC 1010/Citric acid, sodium salt | 200/200 ppm | 0 |
| BTC 1010/Nitrilotriacetic acid, trisodium salt | 200/200 ppm | 0 |
| BTC 1010/Nitrilotriphosphonic acid, trisodium salt | 200/200 ppm | 0 |

*Active ingredient
EDTA salt = tetrasodium salt of EDTA;
DGH = n-dodecylguanidine hydrochloride

EXAMPLE 3

The preservative efficacy of several cationic compounds, with and without the addition of EDTA salt, to control and inhibit the growth of mold and yeast in a VAE copolymer emulsion, stabilized with nonionic surfactants and containing less than 1000 ppm vinyl acetate was assessed according to the following procedure:

Yeasts

*Rhodoturula glutinis, Candida guillermondi*, and *Candida tropicalis*, Molds: *Geotrichum candidum, Aspergillus* species, *Sporothrix* species, *Trichoderma viride*, and *Cladosporium* species.

Mixed Yeast Inoculum Preparation

Each yeast culture was individually grown on potato dextrose agar plates by inoculating the agar surface. The potato dextrose agar plates were then incubated for 3-7 days at 25° C. After this incubation period, the yeast cells were harvested using quarter strength Ringers solution to wash the colonies off the agar surface. The washings were combined into a sterile, Erlenmeyer flask. The number of plates used and the amount of Ringers solution used to wash off the cells is adjusted during the procedure to ultimately obtain a final microbial count in the range of $10^6$-$10^7$ CFU/mL.

Mixed Mold Inoculum Preparation

Each mold culture was individually grown on potato dextrose agar plates by inoculating the agar surface. The potato dextrose agar plates were then incubated for 3-7 days at 25° C. After this incubation period, the mold cells were harvested using a 0.005% dioctyl sulfosuccinate aqueous solution to wash the colonies off the agar surface. The washings were filtered through sterile cheesecloth and the filtrates combined into one sterile, Erlenmeyer flask. The number of plates used and the amount of 0.005% dioctyl sulfosuccinate used to wash off the cells is adjusted during the procedure to obtain a final microbial count in the range of $10^6$-$10^7$ CFU/mL.

Fungal Biochallenge Test Procedure

Each test sample (50 g) of polymer emulsion containing a test antimicrobial agent was inoculated with 0.5 mL of the mixed yeast inoculum. After mixing well, the opened sample containers were then placed into a larger second container containing 20 g of sterile vermiculite and 80 g of sterile water. Each test sample was then inoculated with 0.5 mL of the mixed mold inoculum by gently distributing the mold inoculum over the entire surface of the emulsion test sample. The samples were not mixed further. With minimal disturbance of the test sample surfaces, covers were placed onto the larger vermiculite containers leaving the smaller emulsion test sample container open inside the vermiculite container. The samples were then incubated for 28 days at 25° C. After the 28 day incubation period, the vermiculite containers were opened without disturbing the test sample surfaces and the presence of any surface fungal growth was visually assessed. After recording these observations as no growth, slight growth, moderate growth, heavy growth, or dense growth, the samples were thoroughly mixed and each was streak plated onto potato dextrose agar (PDA) to assess the level of surviving microorganisms. The potato dextrose agar plates were incubated at 25° C. for 3-5 days before growth assessment.

Table 3 displays the preservative efficacy data of specific cationic compounds, with and without the addition of EDTA salt, against yeasts and molds in Airflex 410 VAE polymer emulsion. Both the cationic compounds by themselves and EDTA salt by itself offer no protection against the growth of yeasts and molds. However, when EDTA salt is used in combination with either Vantocil IB or BTC 1010 cationics, yeast and mold growth is unexpectedly inhibited and the emulsion sample is adequately preserved against these microorganisms.

TABLE 3

| Biocide | Surface Fungal Growth | Growth on PDA |
| --- | --- | --- |
| Blank (no biocide) | Dense Growth | Dense |
| 200 ppm EDTA salt | Slight Growth | Dense |
| 200 ppm Vantocil IB | Slight Growth | Dense |
| 200 ppm BTC 1010 | Moderate Growth | Dense |
| 100 ppm Vantocil IB/ 100 ppm EDTA salt | Slight Growth | No Growth |
| 300 ppm BTC 1010/ 200 ppm EDTA salt | Slight Growth | No Growth |
| 200 ppm BTC 1010/ 200 ppm EDTA salt | Slight Growth | Dense |

EDTA salt = tetrasodium salt of EDTA

What is claimed is:

1. An aqueous surfactant stabilized polymer emulsion composition resistant to biodeteriogenic microbe contamination comprising an aqueous polymer emulsion combined with a cationic compound and an ethylenediamine acid compound having the structure:

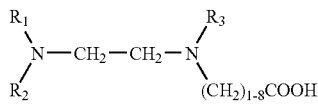

wherein $R_1$, $R_2$, and $R_3$ are, independently, H, a $C_1$-$C_{12}$ alkyl, a —$(CH_2)_{1-8}COOH$; or a mono-, di-, tri- or tetra-salt of an ethylenediamine acid compound of the above structure; wherein the mono-, di-, tri-, or tetra-salt of the ethylenediamine acid compound is selected from the group consisting of an alkali metal salt, an alkaline earth metal salt, an ammonium salt or an ammonium derived salts having the structure:

wherein $R_4$, $R_5$, $R_6$, and $R_7$ are independently, H or $C_{1-12}$ alkyl; provided the salt is soluble in water; and the cationic compound is selected from the group consisting of a substituted pyridinium salt, a tetraalkylsubstituted ammonium salt, a polymeric biguanide, a biguanide, a polymeric cationic compound, a benzalkonium derivative, and mixtures thereof; wherein the substituted pyridinium salt is substituted with an alkyl, a cycloalkyl, or an aryl group containing 2 to 18 carbons, and each alkyl group in the tetraalkylsubstituted ammonium compound independently contains 1 to 18 carbons, said polymer emulsion containing one or more surfactants or one or more surfactants and anionic constituents; the surfactants selected from the group consisting of anionic surfactants and nonionic surfactants.

2. The polymer emulsion composition of claim 1 wherein the ethylenediamine acid compound is a mono-, di-, tri-, or tetra-salt of ethylenediamine tetraacetic acid.

3. The polymer emulsion composition of claim 1 containing an anionic surfactant, a nonionic surfactant, or both an anionic surfactant and a nonionic surfactant, and the ethylenediamine compound is a tetrasodium salt of ethylenediamine tetraacetic acid.

4. The polymer emulsion composition of claim 1, wherein the cationic compound is selected from the group consisting of poly(hexamethylenebiguanide) hydrochloride, didecyldimethylammonium chloride, cetylpyridinium chloride, chlorhexidine, benzethonium chloride, a mix of $C_{12}$-$C_{18}$ alkyldimethyl benzalkonium chlorides, and mixtures thereof, and the ethylenediamine acid compound is a salt of ethylenediamine tetraacetic acid.

5. The polymer emulsion composition of claim 1 wherein the polymer emulsion is selected from the group consisting of a poly(vinyl acetate-co-ethylene), poly(vinyl acetate), poly(vinyl acetate-butyl acrylate), poly(vinyl acetate-(2-ethyl) hexyl acrylate), a polyacrylic, a polymethacrylic, a poly(styrene-acrylic), and poly(vinyl chloride-co-ethylene).

6. The polymer emulsion composition of claim 1 wherein the polymer emulsion is a poly(vinyl acetate-co-ethylene) or a poly(vinyl acetate).

7. The polymer emulsion composition of claim 1 wherein each of the ethylenediamine acid compound and the cationic compound is present in an amount ranging from 10 ppm to 1 wt %, based on the wet weight of the polymer emulsion.

8. The polymer emulsion composition of claim 1 wherein each of the ethylenediamine acid compound and the cationic compound is present in an amount ranging from 50 ppm to 5000 ppm, based on the wet weight of the polymer emulsion.

9. The polymer emulsion composition of claim 1 wherein each of the ethylenediamine acid compound and the cationic compound is present in an amount ranging from 50 ppm to 500 ppm, based on the wet weight of the polymer emulsion.

10. An aqueous surfactant stabilized polymer emulsion composition resistant to biodeteriogenic microbe contamination comprising an aqueous polymer emulsion combined with a cationic compound and a sodium salt of ethylenediamine tetraacetic acid, said cationic compound selected from the group consisting of poly(hexamethylenebiguanide) hydrochloride, didecyldimethylammonium chloride, cetylpyridinium chloride, chlorhexidine, a mix of $C_{12}$-$C_{18}$ alkyldimethyl benzalkonium chlorides, and mixtures thereof; wherein the polymer emulsion contains one or more surfactants selected from the group consisting of anionic surfactants and nonionic surfactants.

11. A method for preventing biodeteriogenic microbe contamination in polymer emulsions comprising:

combining an aqueous surfactant stabilized polymer emulsion with an effective amount of an ethylenediamine acid compound and a cationic compound; wherein said ethylenediamine acid compound has the structure:

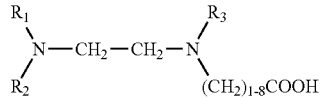

wherein $R_1$, $R_2$, and $R_3$ are, independently, H, a $C_1$-$C_{12}$ alkyl, a —$(CH_2)_{1-8}COOH$; or a mono-, di-, tri- or tetra-salt of an ethylenediamine acid compound of the above structure, wherein the mono-, di-, tri-, or tetra-salt is selected from the group consisting of an alkali metal salt, an alkaline earth metal salt, an ammonium salt or an ammonium derived salts having the structure:

wherein $R_4$, $R_5$, $R_6$, and $R_7$ are independently, H or $C_{1-12}$ alkyl; provided the salt is soluble in water; and the cationic compound is selected from the group consisting of a substituted pyridinium salt, a tetraalkylsubstituted ammonium salt, a polymeric guanide, a polymeric biguanide, a polymeric cationic compound, a benzalkonium derivative, and mixtures thereof, wherein the substituted pyridinium salt is substituted with an alkyl, a cycloalkyl, or an aryl group containing 2 to 18 carbons, and each alkyl group in the tetraalkylsubstituted ammonium compound independently contains 1 to 18 carbons, said polymer emulsion containing one or more surfactants, or one or more surfactants and anionic constituents; the surfactants selected from the group consisting of anionic surfactants and nonionic surfactants.

12. The method of claim 11 wherein the polymer emulsion contains an anionic surfactant, a nonionic surfactant, or both an anionic surfactant and a nonionic surfactant and the ethylenediamine compound is a tetrasodium salt of ethylenediamine tetraacetic acid.

13. The method of claim 11 wherein the cationic compound is selected from the group consisting of poly(hexamethylenebiguanide) hydrochloride, didecyldimethylammonium chloride, cetylpyridinium chloride, chlorhexidine, benzethonium chloride, a mix of $C_{12}$-$C_{18}$ alkyldimethyl benzalkonium chlorides, and mixtures thereof, and the ethylenediamine acid compound is a salt of ethylenediamine tetraacetic acid.

14. The method of claim 11 wherein the polymer emulsion is selected from the group consisting of a poly(vinyl acetate-co-ethylene), poly(vinyl acetate), poly(vinyl acetate-butyl acrylate), poly(vinyl acetate-(2-ethyl)hexyl acrylate), a polyacrylic, a polymethacrylic, a poly(styrene-acrylic), and poly(vinyl chloride-co-ethylene).

15. The method of claim 11 wherein the polymer emulsion is a poly(vinyl acetate-co-ethylene) or a poly(vinyl acetate).

16. The method of claim 11 wherein the amount of each of the ethylenediamine acid compound and the cationic compound ranges from 10 ppm to 1 wt %, based on the wet weight of the polymer emulsion.

17. The method of claim 11 wherein the amount of each of the ethylenediamine acid compound and the cationic compound ranges from 50 ppm to 5000 ppm, based on the wet weight of the polymer emulsion.

18. The method of claim 11 wherein the amount of each of the ethylenediamine acid compound and the cationic compound ranges from 50 ppm to 500 ppm, based on the wet weight of the polymer emulsion.

19. A method for preventing biodeteriogenic microbe contamination in polymer emulsions comprising:
combining an aqueous surfactant stabilized polymer emulsion with an effective amount of a cationic compound and a sodium salt of ethylenediamine tetraacetic acid; said cationic compound selected from the group consisting of poly(hexamethylenebiguanide) hydrochloride, didecyldimethylammonium chloride, cetylpyridinium chloride, chlorhexidine, benzethonium chloride, a mix of $C_{12}$-$C_{18}$ alkyldimethyl benzalkonium chlorides, and mixtures thereof.

20. An adhesive formulation comprising a polymer emulsion composition of claim 1.

21. A coating formulation comprising a polymer emulsion composition of claim 1.

22. An adhesive formulation comprising a polymer emulsion composition of claim 10.

23. A coating formulation comprising a polymer emulsion composition of claim 10.

* * * * *